(12) United States Patent
Aladahalli et al.

(10) Patent No.: US 12,014,823 B2
(45) Date of Patent: Jun. 18, 2024

(54) METHODS AND SYSTEMS FOR COMPUTER-AIDED DIAGNOSIS WITH DEEP LEARNING MODELS

(71) Applicant: GE Precision Healthcare LLC, Milwaukee, WI (US)

(72) Inventors: Chandan Kumar Mallappa Aladahalli, Bangalore (IN); Rakesh Mullick, Bangalore (IN); James William Gualtieri, Glenshaw, PA (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 975 days.

(21) Appl. No.: 16/557,797

(22) Filed: Aug. 30, 2019

(65) Prior Publication Data

US 2021/0065899 A1    Mar. 4, 2021

(51) Int. Cl.
*G16H 50/20* (2018.01)
*G06N 3/08* (2023.01)

(52) U.S. Cl.
CPC ............... *G16H 50/20* (2018.01); *G06N 3/08* (2013.01)

(58) Field of Classification Search
CPC ........ G16H 50/20; G16H 30/20; G16H 30/40; G06N 3/08
See application file for complete search history.

(56) References Cited

U.S. PATENT DOCUMENTS

| | | | |
|---|---|---|---|
| 5,463,548 A | 10/1995 | Asada et al. | |
| 5,839,438 A | 11/1998 | Graettinger et al. | |
| 7,783,094 B2 | 8/2010 | Collins et al. | |
| 9,536,054 B1 | 1/2017 | Podilchuk et al. | |
| 9,589,374 B1 | 3/2017 | Gao et al. | |
| 2016/0259857 A1 | 9/2016 | Wang et al. | |

(Continued)

FOREIGN PATENT DOCUMENTS

| | | | | |
|---|---|---|---|---|
| CA | 3104779 A1 | * | 1/2020 | ......... A61B 1/00009 |
| CN | 106095983 A | | 11/2016 | |

(Continued)

OTHER PUBLICATIONS

International Application No. PCT/US2020/046646 filed Aug. 17, 2020—International Search Report and Written Opinion issued on Oct. 16, 2020; 14 pages.

*Primary Examiner* — Robert A Sorey
*Assistant Examiner* — Kimberly A. Sass
(74) *Attorney, Agent, or Firm* — McCoy Russell LLP

(57) ABSTRACT

Various methods and systems are provided for computer-aided diagnosis. In one embodiment, a method comprises acquiring, with an imaging system, a medical image of a subject, generating, with a radiologist model associated with a radiologist of an institution, a computer-aided diagnosis for the medical image, the radiologist model comprising a deep neural network trained on a plurality of diagnoses provided by the radiologist, displaying, to the radiologist via a display device, the medical image and the computer-aided diagnosis, and selectively updating, based on the medical image, one or more of the radiologist model, an institution model associated with the institution, and a geographic model associated with a geographic area containing the institution. In this way, a radiologist may be assisted by a deep neural network model configured as a digital twin of the radiologist.

18 Claims, 5 Drawing Sheets

(56) References Cited

U.S. PATENT DOCUMENTS

| | | |
|---|---|---|
| 2016/0317127 A1 | 11/2016 | dos Santos Mendonca et al. |
| 2016/0350919 A1 | 12/2016 | Steigauf |
| 2017/0017760 A1* | 1/2017 | Freese .................... G16H 40/63 |
| 2017/0068994 A1 | 3/2017 | Slomkowski et al. |
| 2018/0107796 A1* | 4/2018 | Behar .................... G16H 50/50 |
| 2018/0121576 A1* | 5/2018 | Mosher .................. G06N 20/00 |
| 2019/0005200 A1 | 1/2019 | Zimmerman et al. |
| 2019/0087544 A1 | 3/2019 | Peterson |
| 2019/0164285 A1* | 5/2019 | Nye .......................... G06T 7/70 |
| 2021/0042916 A1* | 2/2021 | Zhang .................... A61B 6/50 |

FOREIGN PATENT DOCUMENTS

| | | |
|---|---|---|
| CN | 106448670 A | 2/2017 |
| KR | 20130082839 A | 7/2013 |
| KR | 101666930 B1 | 10/2016 |

\* cited by examiner

METHODS AND SYSTEMS FOR COMPUTER-AIDED DIAGNOSIS WITH DEEP LEARNING MODELS

FIELD

Embodiments of the subject matter disclosed herein relate to diagnostic imaging, and more particularly, to computer-aided diagnosis for diagnostic imaging.

BACKGROUND

Medical imaging systems are often used to obtain internal physiological information of a subject, such as a patient. For example, a medical imaging system may be used to obtain images of the bone structure, internal organs (e.g., the brain, the heart, the lungs), blood flow through vessels, and various other features of a subject. Medical imaging systems may include magnetic resonance imaging (MRI) systems, computed tomography (CT) systems, x-ray systems, ultrasound systems, nuclear medicine systems, and various other imaging modalities.

Radiologists specialize in diagnosing and treating injuries and diseases using images acquired via such medical imaging systems. Radiologists may be trained to use medical imaging systems to acquire medical images, or may work with imaging technologists who are specially trained to control medical imaging systems to acquire medical images. Radiologist review and interpret medical images to determine a diagnosis.

BRIEF DESCRIPTION

In one embodiment, a method comprises acquiring, with an imaging system, a medical image of a subject, generating, with a radiologist model associated with a radiologist of an institution, a computer-aided diagnosis for the medical image, the radiologist model comprising a deep neural network trained on a plurality of diagnoses provided by the radiologist, displaying, via a display device, the medical image and the computer-aided diagnosis, and selectively updating, based on the medical image, one or more of the radiologist model, an institution model associated with the institution, and a geographic model associated with a geographic area containing the institution. In this way, a radiologist may be assisted by a deep neural network model configured as a digital twin of the radiologist with increased accuracy while avoiding overfitting of the deep neural network model.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
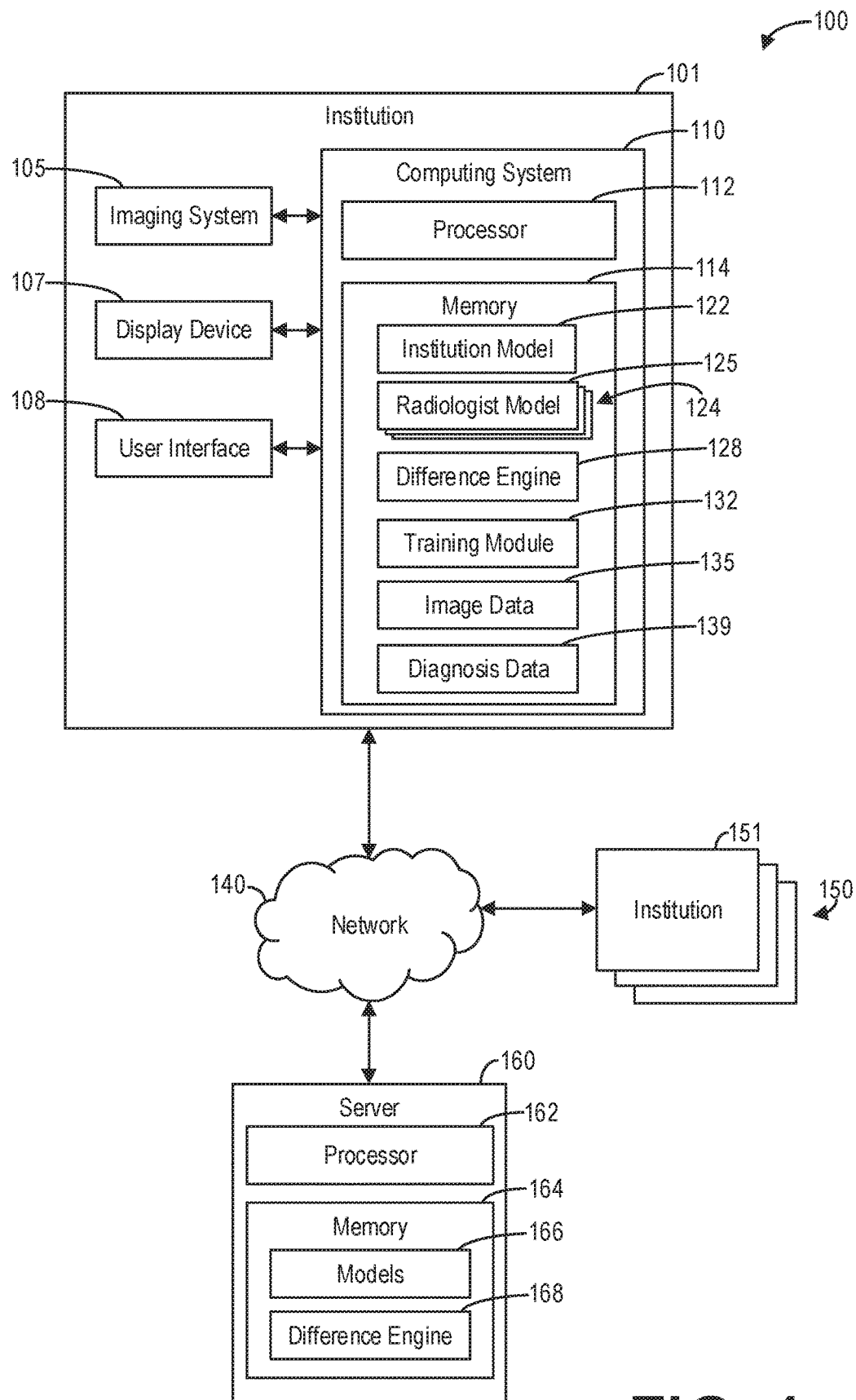
FIG. 1 is a block diagram of a computing environment for an ensemble of deep learning models of radiologists according to an embodiment of the invention.

The following description relates to various embodiments for computer-aided diagnosis with deep learning models. In particular, systems and methods are provided for modeling a radiologist ecosystem with an ensemble of deep neural networks. A system, such as the system depicted in FIG. 1, includes a plurality of institutions, each associated with one or more radiologists, distributed across a plurality of geographic regions with different diagnostic imaging protocols and practices. Although the methodology for diagnostic recommendations is ideally objective, a diagnosis by a radiologist is at the discretion and personal preferences of the radiologist and therefore is ultimately subjective. Diagnostic preferences may vary significantly between radiologists. In order to provide accurate computer-aided diagnoses for radiologists that may accommodate the different preferences among radiologists, an ensemble of continuously-learning deep neural networks may be provided as radiologist digital twins for assisting radiologists in diagnosis. An ensemble of such deep learning models, such as the ensemble of deep learning models depicted in FIG. 2, also includes a deep learning model for each institution, a deep learning model for each geographic region, and a baseline neural network model. The baseline neural network is initially trained on data sourced from a plurality of radiologists, and then is customized to match a radiologist's unique diagnosis methods and preferences. Specifically, the baseline neural network is further customized to geographic-specific models, which are in turn customized to institution-specific models, which are in turn customized to radiologist-specific models. The ensemble of deep neural networks is continuously but selectively trained on imaging and reporting data from a multitude of radiologists from a plurality of institutions and geographies, and thus comprises a digital twin of a radiologist ecosystem. The deep neural networks at each level of the hierarchy in the ensemble are continuously updated based on feedback through corrections to output of the deep neural networks and/or the original annotations and diagnoses of radiologists. The ensemble allows continuous temporal updates and ensemble-wise comparison, which thus allows personalization of radiologist-specific digital twins while maintaining ensemble-level coherence. Further, a method for providing computer-aided diagnosis, such as the method depicted in FIG. 3, further allows a radiologist to access digital twins of other radiologists at other institutions as a "second opinion" to augment the diagnosis of the radiologist and the computer-aided diagnosis of the radiologist's digital twin. A method for updating different levels of the ensemble, such as the method depicted in FIG. 4, includes evaluating the performance of radiologist models, institution models, and geographic models with regard to a diagnosis of a radiologist. The models may be selectively updated and deployed, as depicted in FIG. 5, based on the performances of the models.

FIG. 1 is a block diagram of a computing system 100 for an ensemble of deep learning models of radiologists according to an embodiment of the invention. The computing system 100 includes a computing system 110 of an institution 101, which is communicatively coupled via a network 140 to each institution 151 of a plurality of institutions 150 as well as a server 160. The institution 101 and each institution 151 of the plurality of institutions 150 comprise a medical institution or facility such as a hospital or clinic.

Institution 101 includes an imaging system 105 configured to acquire a medical image of at least a portion of a subject, such as a patient. The imaging system 105 may comprise a medical imaging system such as an x-ray radiography system, an ultrasound imaging system, a computed tomography (CT) imaging system, a nuclear medicine imaging system such as a positron emission tomography (PET) system, a magnetic resonance imaging (MRI) system, and so on. Institution 101 may include a plurality of imaging systems 105 of varying imaging modalities, for example.

Institution 101 further includes a display device 107 configured to display medical images acquired via the imaging system 105 for review by a radiologist of the institution 101. The display device 107 may include one or more display devices utilizing virtually any type of technology. In some embodiments, the display device 107 may comprise a computer monitor, as a non-limiting example. The display device 107 may be combined with one or more of the user interface 108, and the computing system 110 in a shared enclosure, or may be peripheral display devices and may comprise a monitor, touchscreen, projector, or other display device known in the art.

The radiologist may provide, via a user interface 108, user input regarding a medical image displayed via the display device 107, such as a diagnosis, annotations of the medical image, and so on. The user interface 108 may comprise one or more input devices including, but not limited to, a touchscreen, a keyboard, a mouse, a trackpad, a motion sensing camera, or another device configured to enable a user to interact with and manipulate data within a computing system 110 of the institution 101.

The computing system 110 of the institution 101 includes a processor 112 configured to execute machine readable instructions stored in memory 114. Processor 112 may comprise a single core or multi-core processor, and the programs executed thereon may be configured for parallel or distributed processing. In some embodiments, the processor 112 may optionally include individual components that are distributed throughout two or more devices, which may be remotely located and/or configured for coordinated processing. In some embodiments, one or more aspects of the processor 112 may be virtualized and executed by remotely-accessible networked computing devices configured in a cloud computing configuration.

The memory 114 may comprise a non-transitory memory. The memory 114 may further store an institution model 122 of the institution 101, a plurality of radiologist models 124 including at least a radiologist model 125 for a radiologist, a difference engine 128, a training module 132, image data 135 such as medical image data acquired via the imaging system 105, and diagnosis data 139 such as diagnoses for medical images input by radiologists via the user interface 108. The institution model 122 may comprise a deep learning model such as a deep neural network, and may be trained on a set of medical images and a corresponding set of diagnoses for the medical images provided by all radiologists of the institution 101. Each radiologist model 125 of the plurality of radiologist models 124 may also comprise a deep learning model such as a deep neural network, and may be trained on a set of medical images and a corresponding set of diagnoses for the medical images provided by a given radiologist of the institution 101. That is, a dedicated radiologist model 125 may be stored in memory 114 for each radiologist associated with the institution 101. The institution model 122 and each radiologist model 125 of the plurality of radiologist models 124 may include one or more deep neural networks, comprising a plurality of weights and biases, activation functions, loss functions, gradient descent algorithms, and instructions for implementing the one or more deep neural networks to receive medical image data and map the input medical image data to diagnostic output. To that end, the memory 114 may store instructions for implementing a neural network, such as a convolutional neural network (CNN) or another type of neural network architecture.

The radiologist model 125 is thus a digital twin of the radiologist, such that the radiologist model 125 accepts a medical image as input and generates a diagnosis for the medical image as an output, wherein the radiologist model 125 is trained as described herein such that the diagnosis generated by the radiologist model 125 is similar to a diagnosis provided by the radiologist. Similarly, by training the institution model 122 on medical images and diagnoses from all radiologists associated with the institution 101, the institution model 122 is thus a digital twin of the institution 101, such that the institution model 122 accepts a medical image as input and generates a diagnosis for the medical image as an output, wherein the diagnosis generated by the institution model 122 may be similar to a diagnosis provided by all of the radiologists working together.

The memory 114 further includes a difference engine 128 configured to evaluate differences between a diagnosis provided by a radiologist and a computer-aided diagnosis generated by a corresponding radiologist model 125 for the radiologist. As described further herein, the difference engine 128 may evaluate, based on such differences, whether to update one or more of the deep learning models. Further, in some examples, the difference engine 128 may be configured to evaluate the performance of other deep learning models, such as the institution model 122 and/or a geographic model (not shown), in order to determine whether the deep learning models should be updated. An example method for the difference engine 128 is described further herein with regard to FIG. 4.

The training module 132 comprises instructions for training one or more of the deep neural networks stored in the memory 114, such as the institution model 122 and the plurality of radiologist models 124. As an illustrative and non-limiting example, the training module 132 may include instructions that, when executed by the processor 112, cause the processor 112 to update or train the radiologist model 125 of the plurality of radiologist models 124 according to diagnosis data 139 provided by the radiologist corresponding to the radiologist model 125 and image data 135 acquired by the imaging system 105. The training module 132 may update each radiologist model 125 of the plurality of radiologist models 124 after storing a new set of image data 135 and corresponding diagnosis data 139, in some examples, such that each radiologist model 125 is continuously updated, or in other examples the training module 132 may update each radiologist model 125 based on a batch of image data 135 and corresponding diagnosis data 139 after collecting the batch of image data 135 and corresponding diagnosis data 139. The training module 132 may further include various data, such as training data, training routines, or parameters (e.g., weights and biases), associated with one or more neural network models stored in memory 114, for training each radiologist model 125 of the plurality of radiologist models 124 and the embodiments, the memory 114 may include components disposed at two or more devices, which may be remotely located and/or configured for coordinated processing. In some embodiments, one or more aspects of the memory 114 may include remotely-accessible networked storage devices configured in a cloud computing configuration.

It should be understood that the computing environment of the institution 101, including the computing system 110, the display device 107, the user interface 108, and elements of the imaging system 105, are shown in FIG. 1 for illustration, not for limitation. Another appropriate computing environment may include more, fewer, or different components for implementing the methods described further herein.

Further, as mentioned above, the computing system 100 of FIG. 1 further includes a plurality of institutions 150. Each institution 151 of the plurality of institutions 150 may be configured similarly to the institution 101, such that each institution 151 also includes a computing system, imaging system, display device, and user interface similar to the computing system 110, the imaging system 105, the display device 107, and the user interface 108 of the institution 101. Each institution 151 may thus be configured with an institution model similar to institution model 122 of the institution 101, as well as a plurality of radiologist models similar to the plurality of radiologist models 124.

As discussed further herein, in some examples, a radiologist of an institution such as the institution 101 may request a "second opinion" from another radiologist of the institution 101, for example, or even from an institution 151 of the plurality of institutions 150. For example, the patient may suggest visiting a second radiologist at a second institution to obtain a second opinion regarding the diagnosis. The radiologist may thus request, via the user interface 108, the second opinion comprising a second computer-aided diagnosis generated by a radiologist model for the second radiologist. The second computer-aided diagnosis may be transmitted to the computing system 110 via the network 140 from the corresponding institution 151 of the plurality of institutions 150, and displayed via the display device 107. As each institution 151 of the plurality of institutions 150 may be distributed over a large geographic area or even throughout the world, the computing system 100 thus provides the ability to easily obtain the "second opinion" of a second radiologist located at another institution, without the need for the patient to visit the second institution or even the need for the second radiologist to provide the second diagnosis.

The computing system 100 further includes a server 160 communicatively coupled to the institution 101 and the plurality of institutions 150 via the network 140. The server 160 includes a processor 162 configured to execute machine readable instructions stored in memory 164. The processor 162 may comprise a single core or multi-core processor, and the programs executed thereon may be configured for parallel or distributed processing. In some embodiments, the processor 162 may optionally include individual components that are distributed throughout two or more devices, which may be remotely located and/or configured for coordinated processing. In some embodiments, one or more aspects of the processor 162 may be virtualized and executed by remotely-accessible networked computing devices configured in a cloud computing configuration.

The memory 164 may comprise a non-transitory memory storing a plurality of models 166 and a difference engine 168. The models 166 may comprise a plurality of deep learning models, including at least one baseline deep learning model, a plurality of geographic models, a plurality of institution models, and a plurality of radiologist models. The difference engine 168 may be configured to evaluate the performance of one or more of the models 166 with respect to one or more other models of the models 166, and to determine whether to deploy one or more of the models 166 to one or more institutions such as the institution 101 or the institution 151 of the plurality of institutions 150.

In some embodiments, the memory 164 may include components disposed at two or more devices, which may be remotely located and/or configured for coordinated processing. In some embodiments, one or more aspects of the memory 164 may include remotely-accessible networked storage devices configured in a cloud computing configuration.

Thus, as described further herein, the server 160 may comprise a central server configured to coordinate model updates and deployment of updated deep learning models among the plurality of institutions 150 and the institution 101. It should be appreciated that the computing system 100 may include a plurality of servers such as server 160. For example, as described further herein, the ensemble of deep learning models may include a plurality of geographic models. In some examples, a server 160 may be provided for each geographic model of the plurality of geographic models, wherein the server 160 provided for each geographic model is located within the geographic region corresponding to the geographic model.

Figure 2:
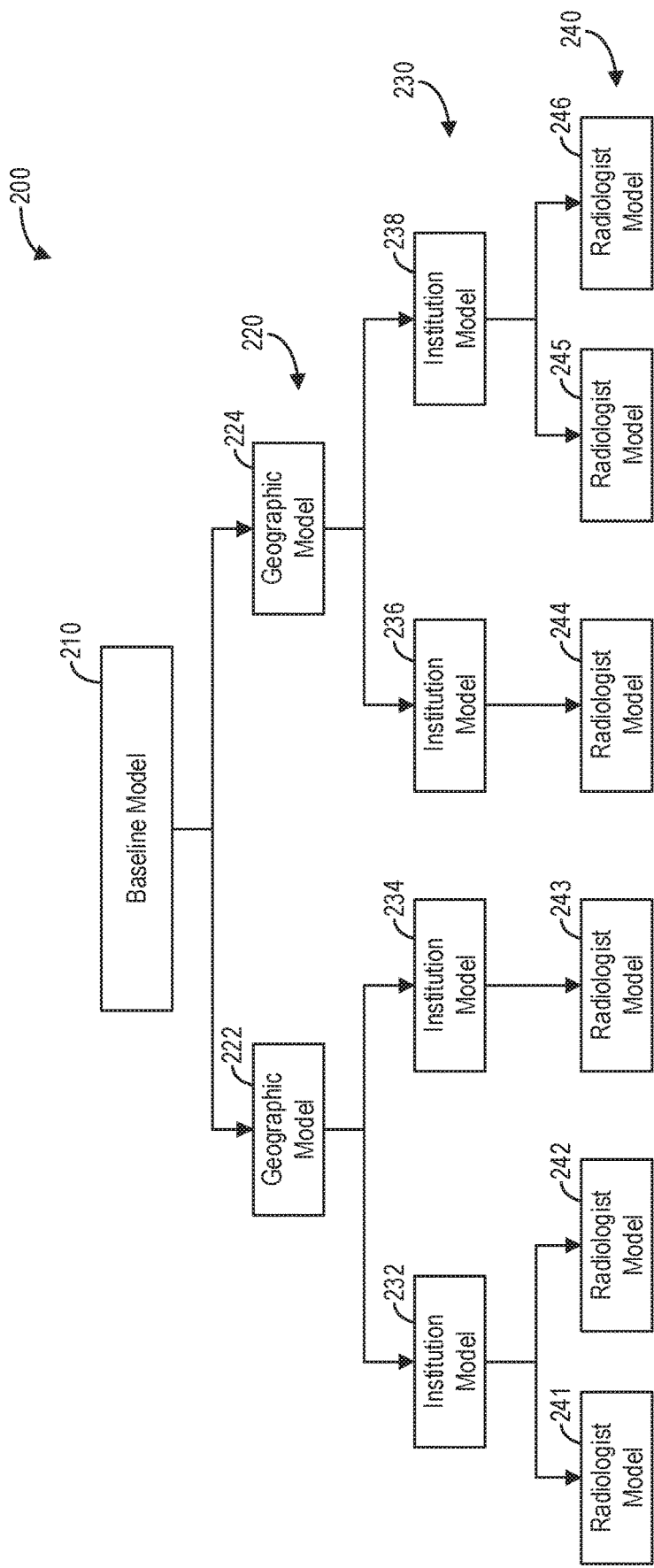
FIG. 2 is a block diagram illustrating an example architecture for an ensemble of deep learning models of radiologists according to an embodiment of the invention.

To further illustrate the ensemble of deep learning models mentioned hereinabove, FIG. 2 is a block diagram illustrating an example architecture for an ensemble 200 of deep learning models of radiologists according to an embodiment of the invention. The ensemble 200 of deep learning models includes a baseline model 210, a plurality of geographic models 220, a plurality of institution models 230, and a plurality of radiologist models 240.

The baseline model 210 comprises a baseline neural network model trained on a diagnosis data sourced from a plurality of radiologists. The baseline model 210 may be duplicated and deployed to initially form a plurality of geographic models 220, a plurality of institution models 230, and a plurality of radiologist models 240.

A first plurality of institutions located in a first geographic area may be assigned a first geographic model 222, while a second plurality of institutions located in a second geographic area may be assigned a second geographic model 224, so that the plurality of geographic models 220 includes at least the first geographic model 222 and the second geographic model 224. The scope of the geographic areas may be determined according to differences in imaging protocols or diagnostic protocols between geographic areas.

The first geographic area includes at least a first institution and a second institution, which are assigned a first institution model 232 and a second institution model 234, respectively. The second geographic area includes at least a third institution and a fourth institution, which are assigned a third institution model 236 and a fourth institution model 238, respectively. Thus, the plurality of institution models 230 includes at least the first institution model 232, the second institution model 234, the third institution model 236, and the fourth institution model 238.

The first institution employs a first radiologist and a second radiologist, who are assigned a first radiologist model 241 and a second radiologist model 242, respectively, while the second institution employs a third radiologist, who is assigned a third radiologist model 243. Similarly, the third institution employs a fourth radiologist who is assigned a fourth radiologist model 244, while the fourth institution employs a fifth radiologist and a sixth radiologist, who are assigned a fifth radiologist model 245 and a sixth radiologist model 246. Thus the plurality of radiologist models 240 includes at least the first radiologist model 241, the second radiologist model 242, the third radiologist model 243, the fourth radiologist model 244, the fifth radiologist model 245, and the sixth radiologist model 246.

As mentioned above, the baseline model 210 may initially be trained on diagnosis data sourced from all of the radiologists, and the baseline model 210 may be deployed as each of the plurality of geographic models 220, each of the institution models 230, and each of the radiologist models 240. As each radiologist provides additional diagnoses, the corresponding radiologist model of the plurality of radiologist models 240 becomes customized to the radiologist. Thus, each radiologist model of the plurality of radiologist models 240 is a digital twin of the corresponding radiologist, such that each radiologist model of the plurality of radiologist models 240 is customized to match the unique diagnosis methods and preferences of a radiologist.

Further, each institution model of the plurality of institution models 230 is updated temporally based on diagnoses of radiologists employed by the institution, such that each institution model comprises a digital twin of the institution. For example, while the first radiologist model 241 is continuously trained on diagnosis data provided by the first radiologist and the second radiologist model 242 is continuously trained on diagnosis data provided by the second radiologist, the first institution model 232 is updated continuously on the diagnosis data from both the first radiologist and the second radiologist.

Similarly, each geographic model of the plurality of geographic models 220 is updated temporally based on diagnoses from the radiologists of the institutions within the corresponding geographic area. For example, while the first institution model 232 is trained on diagnosis data from the first radiologist and the second radiologist and the second institution model 234 is trained on diagnosis data from the third radiologist, the first geographic model 222 is trained on diagnosis data from the first radiologist, the second radiologist, and the third radiologist.

By establishing the ensemble 200 of deep learning models as the baseline model 210, the plurality of geographic models 220, the plurality of institution models 230, and the plurality of institution models 240, the performance of a given model may be evaluated with respect to the performance of other models. For example, the performance of a given radiologist model may be evaluated with respect to the performance of the institution model and the geographic model associated with the radiologist. By evaluating the performance of the radiologist model in this way, a divergence in radiologist performance may be detected. For example, if a radiologist is underperforming (e.g., by making a number of diagnostic errors or omitting annotations that other radiologists would typically provide) with respect to other radiologists within an institution, the performance of the radiologist model for the radiologist may substantially diverge from the performance of the institution model of the institution. In this way, the underperformance of the radiologist may be detected and actions may be taken to improve the performance of the radiologist. Similarly, if a particular radiologist is outperforming (e.g., by providing more accurate diagnoses and more detailed annotations) with respect to other radiologists, the performance of the radiologist model for the radiologist may also substantially diverge from the performance of the institution model of the institution. As the exceptional performance of such a radiologist model is propagated through the ensemble 200, other radiologist models ultimately benefit from the improved performance of the radiologist model. Furthermore, by propagating the customized updates of individual radiologist models throughout the ensemble 200, for example by applying ensemble-wise updates, overfitting may be avoided, thereby improving the performance of all radiologist models in general.

It should be appreciated that the number of geographic models 220, the number of institution models 230, and the number of radiologist models 240 depicted in FIG. 2 are illustrative and non-limiting. In practice, the ensemble 200 may include a much larger plurality of geographic models 220, institution models 230, and radiologist models 240.

Further, each deep learning model of the ensemble 200 may comprise a deep neural network, such as a convolution neural network. For example, the deep learning models of the ensemble 200 may be configured with a convolutional neural network architecture such as a U-net architecture. However, it should be appreciated that the ensemble 200 may be configured with other deep learning model architectures, combinations of deep neural network architectures, and so on. Further, in some examples, the deep learning models may be further configured with natural language processing systems for providing computer-aided diagnoses with natural language components.

Figure 3:
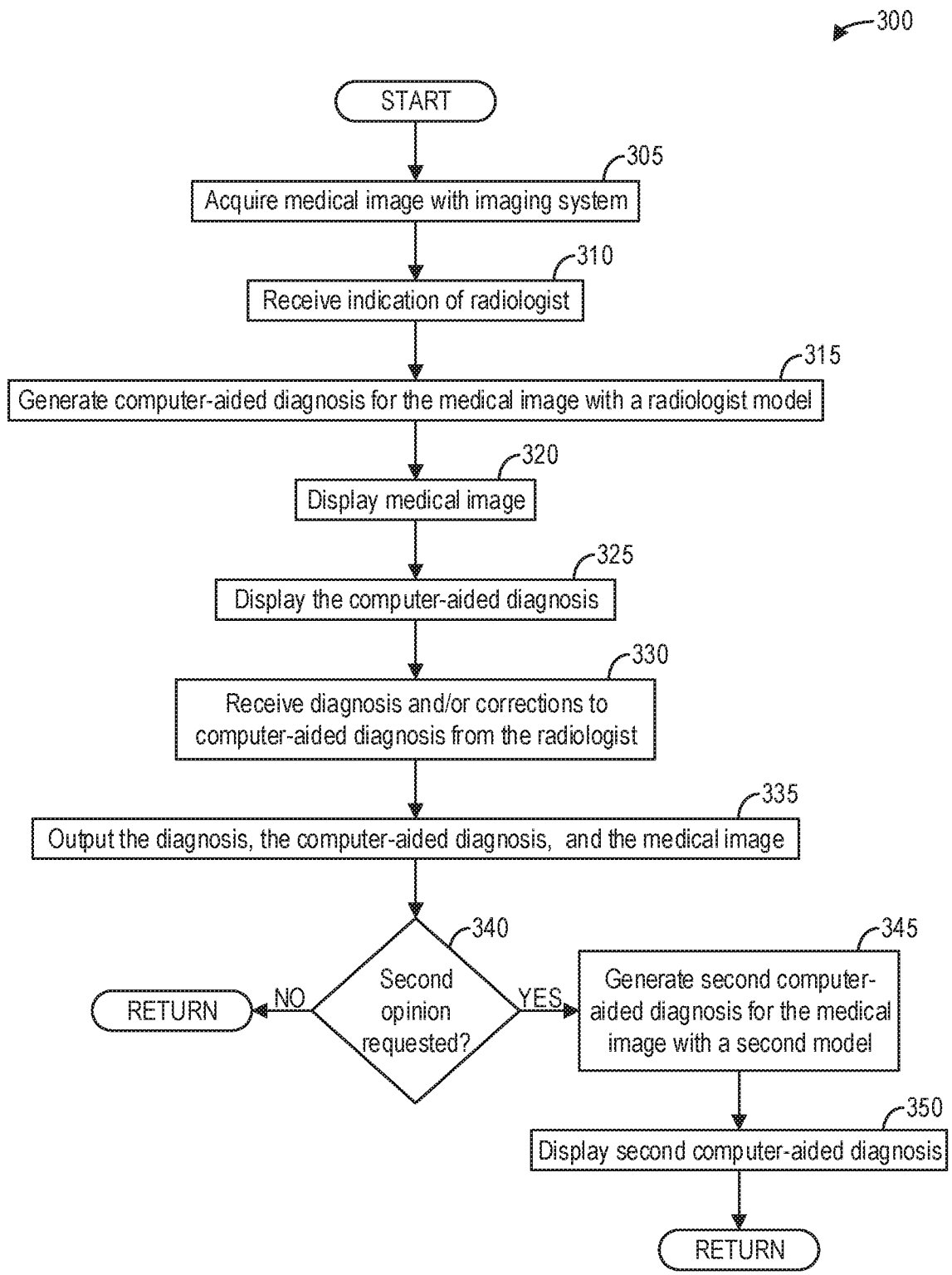
FIG. 3 is a high-level flow chart illustrating an example method for providing computer-aided diagnosis with a deep learning model of a radiologist according to an embodiment of the invention.

FIG. 3 is a high-level flow chart illustrating an example method 300 for providing computer-aided diagnosis with a deep learning model of a radiologist according to an embodiment of the invention. In particular, method 300 relates to generating a computer-aided diagnosis with a radiologist model and receiving feedback from the radiologist for updating the radiologist model. Method 300 is described with regard to the systems and components of FIGS. 1 and 2, though it should be appreciated that the method 300 may be implemented with other systems and components without departing from the scope of the present disclosure. For example, method 300 may be carried out by a computing system, such as computing system 110, of an institution, such as institution 101. Method 300 may be stored as executable instructions in non-transitory memory, such as memory 114 of the computing system 110, and may be executed by a processor, such as processor 112 of the computing system 110, to perform the actions described herein.

Method 300 begins at 305. At 305, method 300 acquires a medical image with an imaging system. For example, method 300 may control the imaging system 105 to acquire a medical image of a patient. As another example, method 300 may retrieve the medical image of the patient acquired via the imaging system 105, which may be stored as image data 135.

At 310, method 300 receives an indication of a radiologist. The radiologist indicated comprises a radiologist who intends to review the medical image. Therefore, the indication of the radiologist may be received via the user interface 108 as user input by the radiologist. As another example, method 300 may determine which radiologist is accessing the medical image for review, for example based on user login information stored in the memory 114.

At 315, method 300 generates a computer-aided diagnosis for the medical image with a radiologist model associated with the radiologist. For example, method 300 may select the radiologist model 125 from the plurality of radiologist models 124 based on the indication of the radiologist, and input the medical image to the radiologist model 125. The radiologist model 125 processes the medical image and outputs the computer-aided diagnosis.

At 320, method 300 displays the medical image, for example via the display device 107, for the radiologist to review. Further, at 325, method 300 displays the computer-aided diagnosis for the radiologist to review. The computer-aided diagnosis may be displayed via the display device 107. Furthermore, the computer-aided diagnosis may be displayed adjacent to the medical image or superimposed on the medical image.

At 330, method 300 receives a diagnosis from the radiologist and/or corrections or annotations to the computer-aided diagnosis from the radiologist. For example, after reviewing the medical image and the computer-aided diagnosis, the radiologist may input the diagnosis and/or corrections or annotations to the computer-aided diagnosis via the user interface 108.

At 335, method 300 outputs the diagnosis, the computer-aided diagnosis, and the medical image. For example, the diagnosis, the computer-aided diagnosis, and the medical image may be output to memory 114 for storage. Additionally, method 300 may output the diagnosis, the computer-aided diagnosis, and the medical image to the difference engine 128 for evaluating the performance of the radiologist model 125 and potentially updating the radiologist model 125 with the training module 132.

Continuing at 340, method 300 determines whether a second opinion is requested. For example, the radiologist may request a second opinion via the user interface 108, wherein the second opinion comprises a second computer-aided diagnosis by a second radiologist model. The request for the second opinion may specify a second radiologist, in some examples, such that the second computer-aided diagnosis may be generated by a radiologist model associated with the second radiologist. The second radiologist may be selected by the radiologist from a plurality of radiologists associated with the institution with which the radiologist is associated, or may be selected from a plurality of radiologists associated with another institution. As another example, the radiologist may specify a particular institution, such that the second computer-aided diagnosis may be generated by a radiologist model associated with the institution or the institution model associated with the institution. In some examples, the request may not include a specification of a particular radiologist or institution for the second opinion, and a default model may be used to generate the second opinion.

If a second opinion is not requested ("NO") at 340, method 300 returns. However, if a second opinion is requested ("YES"), method 300 continues to 345. At 345, method 300 generates a second computer-aided diagnosis for the medical image with a second model. As described above, the second model may comprise a second radiologist model associated with a second radiologist specified in the request for the second opinion, an institution model associated with a second institution specified in the request, or a default model.

After generating the second computer-aided diagnosis with the second model, method 300 continues to 350. At 350, method 300 displays the second computer-aided diagnosis, for example via the display device 107. Method 300 may further output the second computer-aided diagnosis to memory 114 for storage. Method 300 then returns.

Figure 4:
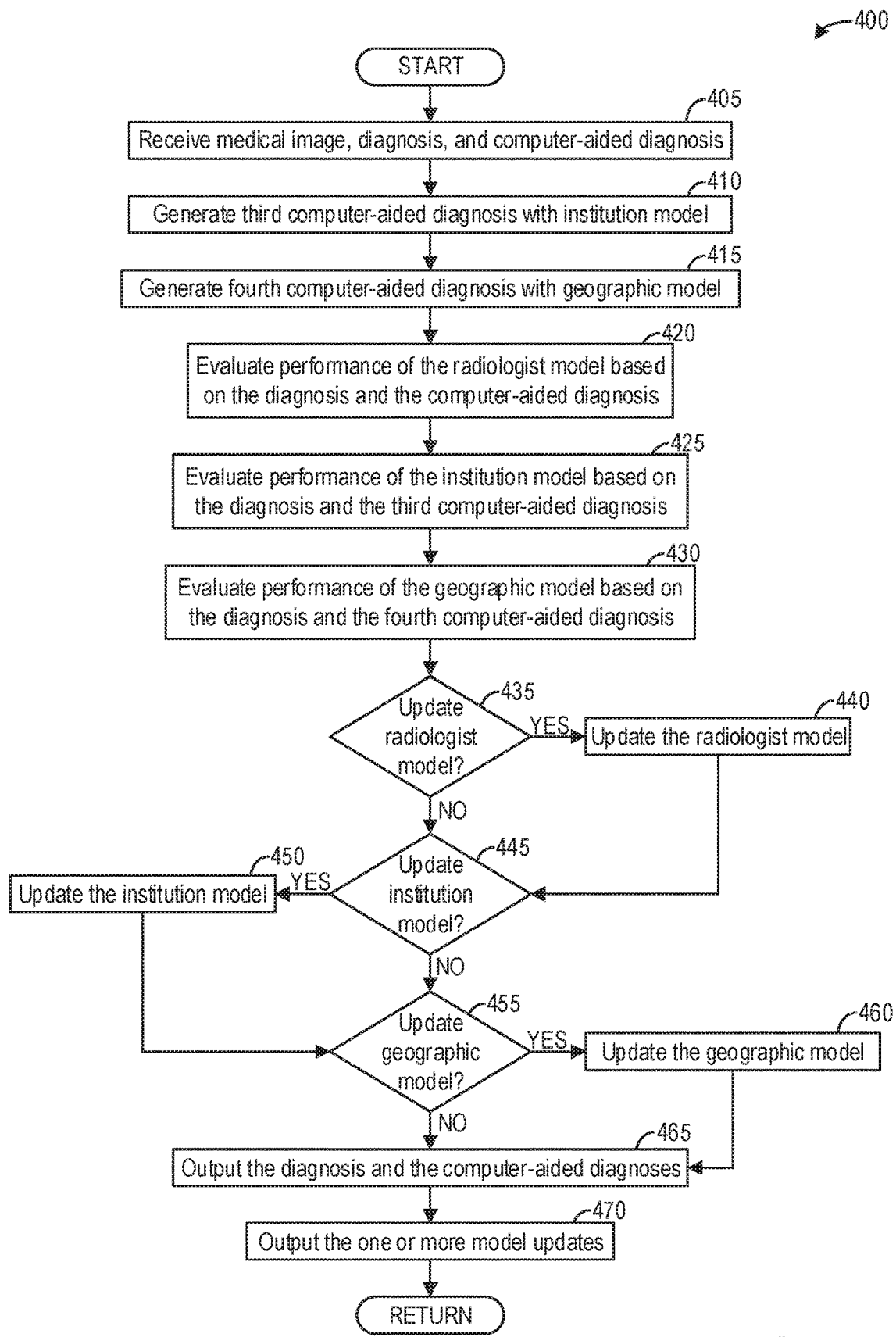
FIG. 4 is a high-level flow chart illustrating an example method for updating one or more models in an ensemble of deep learning models of radiologists according to an embodiment of the invention.
Figure 5:
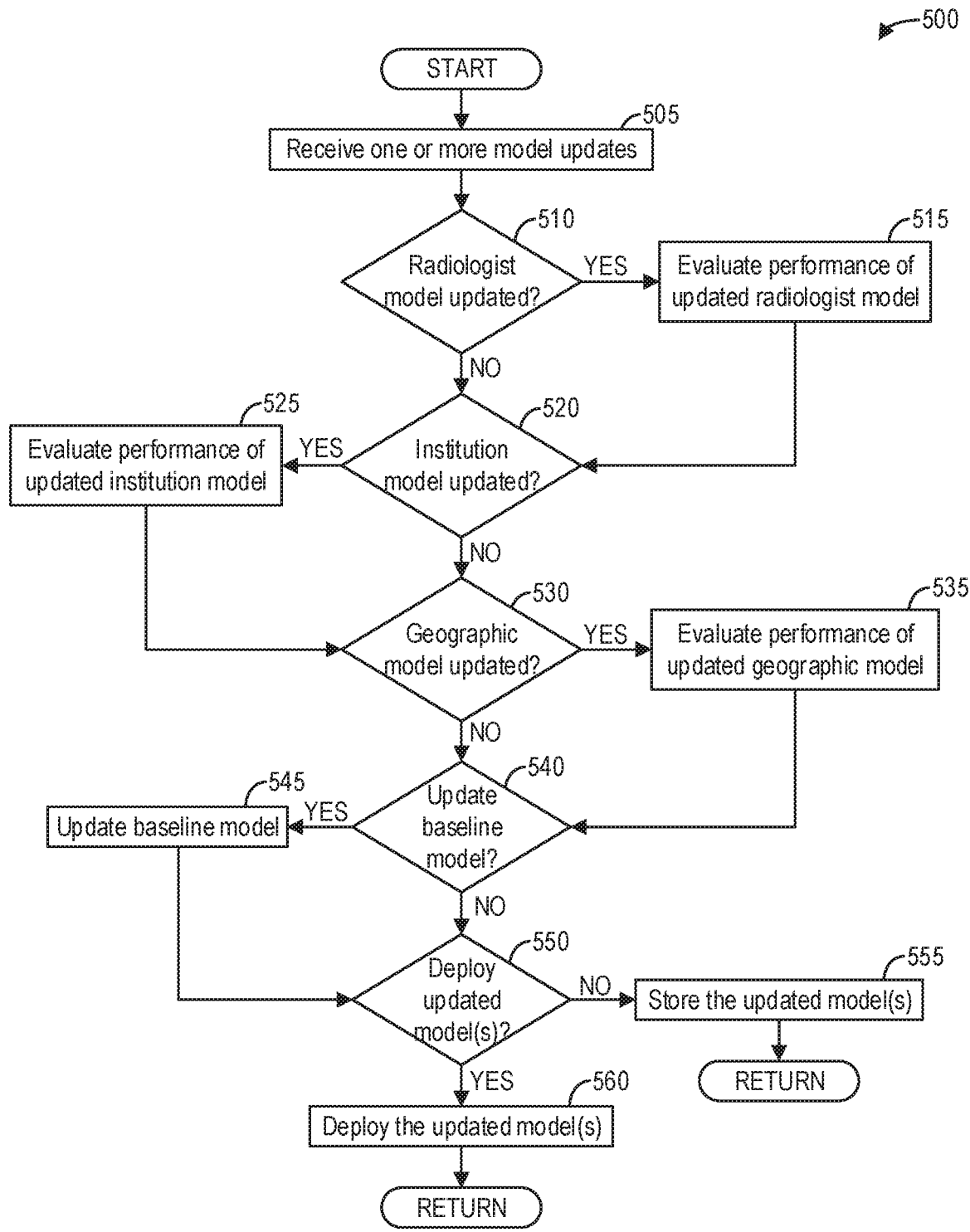
FIG. 5 is a high-level flow chart illustrating an example method for deploying one or more updated deep learning models of radiologists according to an embodiment of the invention.

FIG. 4 is a high-level flow chart illustrating an example method 400 for updating one or more models in an ensemble of deep learning models of radiologists according to an embodiment of the invention. In particular, method 400 relates to evaluating the performance of one or more deep learning models in the ensemble based on the feedback from a radiologist for at least one computer-aided diagnosis, and updating one or more of the deep learning models accordingly. Method 400 is described with regard to the systems and components of FIGS. 1 and 2, though it should be appreciated that the method 400 may be implemented with other systems and components without departing from the scope of the present disclosure. Method 400 may be carried out by a computing system, such as computing system 110, of an institution, such as institution 101. Additionally, portions of method 400 may be carried out by a computing system 110 of an institution 101, while other portions of method 400 may be carried out by a central server, such as server 160, located remotely from the institution 101.

Method 400 begins at 405. At 405, method 400 receives the medical image, a diagnosis associated with the medical image and provided by a radiologist, and a computer-aided diagnosis generated by inputting the medical image to a radiologist model associated with the radiologist. For example, method 400 may receive the medical image, the diagnosis, and the computer-aided diagnosis output at 335 as described hereinabove.

At 410, method 400 generates a third computer-aided diagnosis with an institution model associated with the radiologist. For example, method 400 may generate the third computer-aided diagnosis by inputting the medical image to the institution model for an institution associated with the radiologist. The computer-aided diagnosis output by the institution model is referred to herein as the "third" computer-aided diagnosis to distinguish the computer-aided diagnosis from the computer-aided diagnosis generated by the radiologist model at 315 as well as the second computer-aided diagnosis optionally generated by the second model at 345.

Continuing at 415, method 400 generates a fourth computer-aided diagnosis with a geographic model associated with the radiologist. For example, method 400 may generate the fourth computer-aided diagnosis by inputting the medical image to the geographic model for the geographic area associated with the radiologist. Similar to the third computer-aided diagnosis, the computer-aided diagnosis output by the geographic model is referred to herein as the "fourth" computer-aided diagnosis to distinguish the computer-aided diagnosis from the computer-aided diagnosis generated by the radiologist model at 315, the second computer-aided diagnosis optionally generated by the second model at 345, and the third computer-aided diagnosis generated at 410 by the institution model.

After obtaining the additional computer-aided diagnoses with the institution model and the geographic model, method 400 proceeds to evaluate the performance of each of the deep learning models based on the diagnosis provided by the radiologist. To that end, at 420, method 400 evaluates the performance of the radiologist model based on the diagnosis and the computer-aided diagnosis. For example, method 400 may calculate the difference between the diagnosis and the computer-aided diagnosis. It should be appreciated that the particular approach to evaluating the performance of the radiologist model may depend on the type of computer-aided diagnosis. As a non-limiting and illustrative example, the computer-aided diagnosis may comprise a detection or classification of a lesion in the medical image as well as an indication of the position of the lesion, if detected, in the medical image. The diagnosis may similarly include an observation of a lesion in the medical image as well as an annotation as to the location of the lesion in the medical image. The performance of the model may therefore include calculating the difference in positions of the lesion as indicated in the computer-aided diagnosis and the diagnosis. If the positions are substantially different, such that the radiologist model incorrectly identified the position of the lesion in the medical image, then method 400 may evaluate the performance of the radiologist model accordingly. As another example, the diagnosis provided by the radiologist may indicate that no lesion is observable in the medical image, which may indicate that the radiologist model was incorrect in detecting a lesion in the medical image. Method 400 may therefore determine that the performance of the radiologist model accordingly. For example, method 400 may calculate a performance score based on the accuracy of the computer-aided diagnosis relative to the diagnosis, wherein a higher score corresponds to a greater accuracy. Alternatively, method 400 may simply calculate the difference in the diagnosis and the computer-aided diagnosis, in instances where a difference is calculable. In such an example, a smaller difference corresponds to a greater accuracy of the radiologist model.

Continuing at 425, method 400 evaluates the performance of the institution model based on the diagnosis and the third computer-aided diagnosis, and at 430, method 400 evaluates the performance of the geographic model based on the diagnosis and the fourth computer-aided diagnosis. Method 400 may evaluate the performance of the institution model and the geographic model similar to the evaluation of the performance of the radiologist model as described hereinabove.

At 435, method 400 determines whether to update the radiologist model. The radiologist model may be updated based on the medical image and the diagnosis, for example, if the computer-aided diagnosis was inaccurate, as indicated by the performance score or the difference between the computer-aided diagnosis and the diagnosis as discussed hereinabove. Method 400 may use a threshold performance for the radiologist model to determine whether to update the radiologist model. For example, if the performance of the radiologist model is below the threshold performance for the radiologist model, then the radiologist model may be updated. However, in some examples, the radiologist model may also be updated even if the performance of the radiologist model is perfect, such that there is no difference between the diagnosis and the computer-aided diagnosis. If the radiologist model is not to be updated ("NO"), method 400 continues to 445. However, if the radiologist model is to be updated ("YES"), method 400 continues to 440. At 440, method 400 updates the radiologist model. Updating the radiologist model may include training the radiologist model on the medical image and the diagnosis, for example. After updating the radiologist model, method 400 continues to 445.

At 445, method 400 determines whether to update the institution model. The institution model may be updated based on the performance of the institution model with regard to the diagnosis. For example, method 400 may also use a threshold performance for the institution model, similar to the threshold performance of the radiologist model described hereinabove, wherein method 400 determines to update the institution model when the performance of the institution model is below the threshold performance for the institution model. However, in some examples, the threshold performance for the institution model may be different than the threshold performance for the radiologist model, in that the threshold performance for the institution model may be evaluated against the performance of the radiologist model. For example, method 400 may determine to update the institution model when the performance of the radiologist model substantially diverges from the performance of the institution model. If the institution model is not to be updated ("NO"), method 400 continues to 455. However, if the institution model is to be updated ("YES"), method 400 continues to 450. At 450, method 400 updates the institution model. Method 400 may update the institution model based on the medical image and the diagnosis, for example by training the institution model on the medical image and the diagnosis. In some examples, method 400 may further train the institution model on other medical image and diagnoses previously used for training the radiologist model but not the institution model. After updating the institution model, method 400 continues to 455.

At 455, method 400 determines whether to update the geographic model.

The geographic model may be updated based on the medical image and the diagnosis, for example as described hereinabove, based on the performance of the geographic model with regard to the diagnosis. For example, method 400 may also use a threshold performance for the geographic model, similar to the threshold performance for the institution model, wherein method 400 may determine to update the geographic model when the performance of the geographic model is below the threshold performance for the geographic model. The threshold performance for the geographic model may be different from the threshold performance for the radiologist model and the threshold performance for the institution model, in that the performance of the institution model may be compared to the threshold performance for the geographic model to determine whether to update the geographic model. For example, if the performance of the institution model is substantially diverging from the performance of the geographic model, and is below the threshold performance for the geographic model, method 400 may determine to update the geographic model. If the geographic model is not to be updated ("NO"), method 400 continues to 465. However, if the geographic model is to be updated ("YES"), method 400 continues to 460. At 460, method 400 updates the geographic model. Method 400 may update the geographic model based on the medical image and the diagnosis, for example by training the geographic model on the medical image and the diagnosis. In some examples, method 400 may further train the geographic model on other medical image and diagnoses previously used for training the radiologist model and/or the institution model but not the geographic model. In this way, updates to lower-level models of the ensemble, such as the radiologist model and the institution model, may eventually be propagated to the higher-level models of the ensemble, such as the geographic model. After updating the geographic model, method 400 continues to 465.

At 465, method 400 outputs the diagnosis and the computer-aided diagnoses. The diagnosis and computer-aided diagnoses may be output to memory, such as memory 114 of the computing system 110 in the institution 101, as an example. Additionally or alternatively, the diagnosis and computer-aided diagnoses may be output to the server 160 for storage and/or additional evaluation and training of deep learning models in the ensemble.

At 470, method 400 outputs the one or more model updates, if any of the models were updated. For example, any updated models may be stored in memory 114 of the computing system 110 such that the updated models may be used for generating computer-aided diagnoses. Additionally, the one or more model updates may be output to the server 160 to be stored and/or used for evaluating and training as discussed further herein with regard to FIG. 5. Method 400 then returns.

FIG. 5 is a high-level flow chart illustrating an example method 500 for deploying one or more updated deep learning models of radiologists according to an embodiment of the invention. In particular, method 500 relates to evaluating updated deep learning models to determine whether to deploy the updated deep learning models within the ensemble of deep learning models. Method 500 is described with regard to the systems and components of FIGS. 1 and 2, though it should be appreciated that the method 500 may be implemented with other systems and components without departing from the scope of the present disclosure. For example, method 500 may be implemented as executable instructions in non-transitory memory, such as memory 164, and executed by a processor, such as processor 162, of a server such as server 160.

Method 500 begins at 505. At 505, method 500 receives one or more model updates. Method 500 may receive the one or more model updates output at 470, for example, corresponding to model updates to one or more of a radiologist model, an institution model, and a geographic model.

Continuing at 510, method 500 determines whether the radiologist model was updated. If the radiologist model was not updated ("NO"), method 500 continues to 520. However, if the radiologist model was updated ("YES"), method 500 continues to 515. At 515, method 500 evaluates the performance of the updated radiologist model. Method 500 may evaluate the performance of the updated radiologist model by using a dedicated evaluation data set comprising a plurality of medical images and corresponding diagnoses, for example. That is, method 500 may input the plurality of medical images of the evaluation data set to the updated radiologist model, and compare corresponding computer-aided diagnoses output by the updated radiologist model to the known diagnoses of the evaluation data set. Method 500 thus may determine whether the updated radiologist model is improved with respect to the radiologist model prior to updating. Method 500 then proceeds to 520.

At 520, method 500 determines whether the institution model was updated. If the institution model was not updated ("NO"), method 500 continues to 530. However, if the institution model was updated ("YES"), method 500 continues to 525. At 525, method 500 evaluates the performance of the updated institution model. The performance of the updated institution model may be evaluated similar to the updated radiologist model as described hereinabove, with the evaluation data set. Method 500 may further determine whether the performance of the updated institution model is improved with respect to the institution model prior to updating. Method 500 then proceeds to 530.

At 530, method 500 determines whether the geographic model was updated. If the geographic model was not updated ("NO"), method 500 continues to 540. However, if the geographic model was updated ("YES"), method 500 continues to 535. At 535, method 500 evaluates the performance of the updated geographic model. The performance of the updated geographic model may be evaluated similar to the updated radiologist model as described hereinabove, with the evaluation data set. Method 500 may further determine whether the updated geographic model is improved with respect to the geographic model prior to the updating. Method 500 then proceeds to 540.

At 540, method 500 determines whether to update the baseline model. Method 500 may determine to update the baseline model if the performance of one or more of the updated models is improved, for example. If the baseline model is not to be updated, method 500 continues to 550. However, if the baseline model is to be updated, method 500 continues to 545. At 545, method 500 updates the baseline model. Method 500 may update the baseline model by incorporating the one or more model updates into the baseline model. As another example, method 500 may update the baseline model by training the baseline model on the same medical images and diagnoses used to obtain the one or more model updates. Method 500 then proceeds to 550.

At 550, method 500 determines whether to deploy one or more of the updated models. Method 500 may determine to deploy an updated model if the performance of the updated model is improved. For example, if the performance of the updated radiologist model is improved while the performance of the updated institution model is not improved, method 500 may determine to deploy the updated radiologist model to replace the radiologist model but not to deploy the updated institution model. In some examples, method 500 may determine to deploy one of the one or more updated models responsive to a request by an institution to update a particular model. Additionally or alternatively, method 500 may determine to deploy one of the one or more updated models based on an elapsed time since a previous deployment of an updated model. For example, method 500 may be configured to deploy updated models on a regular basis, such as once a month or once a year. In this way, updated models may be adequately tested and trained on a sufficient amount of data before deployment. If one or more of the one or more updated models is not to be deployed ("NO"), method 500 continues to 555. At 555, method 500 stores the one or more updated models not to be deployed. For example, method 500 may store the one or more updated models not to be deployed in the memory 164. Method 500 may also store one or more updated models to be deployed in the memory 164. Method 500 then returns.

Further, if one or more of the one or more updated models is to be deployed ("YES"), method 500 continues to 560. At 560, method 500 deploys the one or more updated models to be deployed. For example, if the updated radiologist model is to be deployed, method 500 transmits the updated radiologist model to the institution for use. Alternatively, as the updated radiologist model may already be stored at the institution, method 500 may transmit an indication to use the updated radiologist model in place of the previous radiologist model. Method 500 then returns.

A technical effect of the present disclosure includes the automatic generation of a diagnosis of a medical image with a computing system. Another technical effect of the present disclosure includes the display of an automatically generated diagnosis of a medical image. Yet another technical effect of the present disclosure includes the display of an automatically generated diagnosis of a medical image corresponding to the diagnostic preferences of a radiologist located in another geographic area, without input by the radiologist. Another technical effect of the present disclosure includes the training of an ensemble of deep neural network models configured as digital twins of radiologists.

In one embodiment, a method comprises acquiring, with an imaging system, a medical image of a subject, generating, with a radiologist model associated with a radiologist of an institution, a computer-aided diagnosis for the medical image, the radiologist model comprising a deep neural network trained on a plurality of diagnoses provided by the radiologist, displaying, via a display device, the medical image and the computer-aided diagnosis, and selectively updating, based on the medical image, one or more of the radiologist model, an institution model associated with the institution, and a geographic model associated with a geographic area containing the institution.

In a first example of the method, the method further comprises generating a second computer-aided diagnosis with a second radiologist model associated with a second radiologist, and displaying, to the radiologist via the display device, the second computer-aided diagnosis. In a second example of the method optionally including the first example, the method further comprises receiving, from the radiologist via a user interface, a diagnosis for the medical image, wherein selectively updating the one or more of the radiologist model, the institution model, and the geographic model based on the medical image comprises selectively updating the one or more of the radiologist model, the institution model, and the geographic model based on the diagnosis and the medical image. In a third example of the method optionally including one or more of the first and second examples, the method further comprises evaluating a performance of the radiologist model based on the diagnosis and the computer-aided diagnosis, wherein selectively updating the one or more of the radiologist model, the institution model, and the geographic model comprises updating the radiologist model based on the medical image and the diagnosis responsive to the performance of the radiologist model below a performance threshold for the radiologist model. In a fourth example of the method optionally including one or more of the first through third examples, the method further comprises generating a third computer-aided diagnosis with the institution model for the medical image, and evaluating a performance of the institution model based on the diagnosis and the third computer-aided diagnosis, wherein selectively updating the one or more of the radiologist model, the institution model, and the geographic model comprises updating the institution model based on the medical image and the diagnosis responsive to the performance of the institution model below a performance threshold for the institution model. In a fifth example of the method optionally including one or more of the first through fourth examples, the method further comprises generating a fourth computer-aided diagnosis with the geographic model for the medical image, and evaluating a performance of the geographic model based on the diagnosis and the fourth computer-aided diagnosis, wherein selectively updating the one or more of the radiologist model, the institution model, and the geographic model comprises updating the geographic model based on the medical image and the diagnosis responsive to the performance of the geographic model below a performance threshold for the geographic model. In a sixth example of the method optionally including one or more of the first through fifth examples, the method further comprises updating a baseline deep neural network model based on the medical image and the diagnosis, wherein the baseline deep neural network model is initially trained on diagnostic decisions of a plurality of radiologists, and wherein the radiologist model, the institution model, and the geographic model are initially generated from the baseline deep neural network model. In a seventh example of the method optionally including one or more of the first through sixth examples, the method further comprises evaluating a performance of the radiologist model with respect to one or more of the institution model and the geographic model.

In another embodiment, a method comprises acquiring, with an imaging system, a medical image of a subject, generating, with a radiologist model associated with a radiologist of an institution, a computer-aided diagnosis for the medical image, the radiologist model comprising a deep neural network trained on a plurality of diagnoses provided by the radiologist, displaying, to the radiologist via a display device, the medical image and the computer-aided diagnosis, receiving, from the radiologist via a user interface, a diagnosis for the medical image, and selectively updating, based on the diagnosis, one or more of the radiologist model, an institution model associated with the institution, and a geographic model associated with a geographic area containing the institution.

In a first example of the method, the method further comprises receiving, from the radiologist via the user interface, a request for a second opinion from a second radiologist, generating a second computer-aided diagnosis with a second radiologist model associated with the second radiologist, and displaying, to the radiologist via the display device, the second computer-aided diagnosis. In a second example of the method optionally including the first example, the method further comprises communicating, via a network, the request to a computing system of a second institution associated with the second radiologist, the second radiologist model stored at the computing system of the second institution, the second computer-aided diagnosis generated with the second radiologist model by the computing system of the second institution, and receiving, from the computing system via the network, the second computer-aided diagnosis. In a third example of the method optionally including one or more of the first and second examples, the method further comprises evaluating a performance of the radiologist model based on the diagnosis and the computer-aided diagnosis, wherein selectively updating one or more of the radiologist model, the institution model, and the geographic model comprises updating the radiologist model based on the medical image and the diagnosis responsive to the performance of the radiologist model below a performance threshold for the radiologist model. In a fourth example of the method optionally including one or more of the first through third examples, the method further comprises generating a third computer-aided diagnosis with the institution model for the medical image, and evaluating a performance of the institution model based on the diagnosis and the third computer-aided diagnosis, wherein selectively updating one or more of the radiologist model, the institution model, and the geographic model comprises updating the institution model based on the medical image and the diagnosis responsive to the performance of the institution model below a performance threshold for the institution model. In a fifth example of the method optionally including one or more of the first through fourth examples, the method further comprises generating a fourth computer-aided diagnosis with the geographic model for the medical image, and evaluating a performance of the geographic model based on the diagnosis and the fourth computer-aided diagnosis, wherein selectively updating one or more of the radiologist model, the institution model, and the geographic model comprises updating the geographic model based on the medical image and the diagnosis responsive to the performance of the geographic model below a performance threshold for the geographic model. In a sixth example of the method optionally including one or more of the first through fifth examples, the method further comprises updating a baseline deep neural network model based on the medical image and the diagnosis, wherein the baseline deep neural network model is initially trained on diagnostic decisions of a plurality of radiologists, and wherein the radiologist model, the institution model, and the geographic model are initially generated from the baseline deep neural network model. In a seventh example of the method optionally including one or more of the first through sixth examples, the method further comprises evaluating a performance of the radiologist model with respect to one or more of the institution model and the geographic model.

In another embodiment, a method comprises training a baseline neural network model on diagnostic decisions of a plurality of radiologists, training the baseline neural network model on diagnostic decisions of a subset of the plurality of radiologists corresponding to a geographic region to generate a geographic model, training the geographic model on diagnosis decisions of a subset of the subset of the plurality of radiologists corresponding to an institution in the geographic region to generate an institution model, training the institution model on diagnostic decisions of a radiologist of the plurality of radiologists, the radiologist associated with the institution in the geographic region, to generate a radiologist model, generating, with the radiologist model, a computer-aided diagnosis for a patient, receiving feedback from the radiologist regarding the computer-aided diagnosis, and selectively updating one or more of the baseline neural network model, the geographic model, the institution model, and the radiologist model based on the feedback.

In a first example of the method, the method further comprises training the baseline neural network model on diagnostic decisions of a second subset of the plurality of radiologists corresponding to a second geographic region to generate a second geographic model, training the second geographic model on diagnostic decisions of a subset of the second subset of the plurality of radiologists corresponding to a second institution in the second geographic region to generate a second institution model, and training the second institution model on diagnostic decisions of a second radiologist of the plurality of radiologists, the second radiologist associated with the second institution in the second geographic region, to generate a second radiologist model. In a second example of the method optionally including the first example, the method further comprises receiving a request for a second opinion from the second radiologist of the plurality of radiologists, and transmitting the request to a computing system of the second institution. In a third example of the method optionally including one or more of the first and second examples, the method further comprises receiving, from the computing system of the second institution, a second computer-aided diagnosis generated by the second radiologist model for the second radiologist, and displaying the second computer-aided diagnosis to the radiologist. In a fourth example of the method optionally including one or more of the first through third examples, selectively updating one or more of the baseline neural network model, the geographic model, the institution model, and the radiologist model based on the feedback comprises evaluating a performance of each of the baseline neural network model, the geographic model, the institution model, and the radiologist model with regard to the feedback, and selectively updating one or more of the baseline neural network model, the geographic model, the institution model, and the radiologist model responsive to the performance below a respective performance threshold. In a fifth example of the method optionally including one or more of the first through fourth examples, the method further comprises evaluating a performance of the radiologist model with respect to a performance of the institution model, the geographic model, and the baseline neural network model to identify a divergence of the radiologist model from one or more of the institution model, the geographic model, and the baseline neural network model.

In yet another embodiment, a system comprises an imaging system configured to acquire a medical image of a subject, a display device configured to display the medical image, and a computing system comprising a processor and a non-transitory memory, the non-transitory memory storing a plurality of neural network models initially trained on diagnostic decisions of a plurality of radiologists, the non-transitory memory configured with instructions that when executed cause the processor to: train a first neural network model of the plurality of neural network models based on diagnostic decisions provided by a first radiologist for a first set of medical images acquired via the imaging system; train a second neural network model of the plurality of neural network models based on diagnostic decisions provided by a second radiologist for a second set of medical images acquired via the imaging system; receive an indication of a radiologist to review the medical image; generate a first computer-aided diagnosis with the first neural network model responsive to the indication of the radiologist indicating the first radiologist; generate a second computer-aided diagnosis with the second neural network model responsive to the indication of the radiologist indicating the second radiologist; and display, via the display device, the first computer-aided diagnosis or the second computer-aided diagnosis with the medical image.

In a first example of the system, the non-transitory memory is further configured with instructions that when executed cause the processor to receive, via a user interface communicatively coupled to the computing system, a diagnosis from the first radiologist or the second radiologist regarding the medical image, and update the first neural network model or the second neural network model based on the diagnosis. In a second example of the system optionally including the first example, the plurality of neural network models further includes a third neural network model continuously trained on the diagnostic decisions of the first radiologist and the diagnostic decisions of the second radiologist. In a third example of the system optionally including one or more of the first and second examples, the non-transitory memory is further configured with instructions that when executed cause the processor to evaluate a performance of the first neural network model and the second neural network model with respect to a performance of the third neural network model, and propagate updates from the third neural network model to one or more of the first neural network model and the second neural network model to prevent overfitting of the one or more of the first neural network model and the second neural network model. In a fourth example of the system optionally including one or more of the first through third examples, the non-transitory memory is further configured with instructions that when executed cause the processor to receive, via a user interface, a request for a third computer-aided diagnosis from a third radiologist. In a fifth example of the system optionally including one or more of the first through fourth examples, the non-transitory memory is further configured with instructions that when executed cause the processor to transmit the request to a second computing system, and receive, from the second computing system, the third computer-aided diagnosis, the third computer-aided diagnosis generated by the second computing system with a neural network model trained on diagnostic decisions of the third radiologist.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
executing instructions in non-transitory memory storing a plurality of neural network models initially trained on diagnostic decisions of a plurality of radiologists via a processor in a computing system, wherein the instructions cause the processor to institute:
training a baseline neural network model on diagnostic decisions of the plurality of radiologists;
training the baseline neural network model on diagnostic decisions of a subset of the plurality of radiologists corresponding to a geographic region to customize the baseline neural network model and generate a geographic model;
training the geographic model on diagnosis decisions of a subset of the subset of the plurality of radiologists corresponding to an institution in the geographic region to customize the geographic model and generate an institution model, wherein a scope of a geographic area in the geographic model is determined according to differences in diagnostic protocols between geographic areas;
training the institution model on diagnostic decisions of a radiologist of the plurality of radiologists, the radiologist associated with the institution in the geographic region, to customize the institution model and generate a radiologist model;
generating, with the radiologist model, a computer-aided diagnosis for a patient;
displaying the computer-aided diagnosis for the patient;
receiving feedback from a radiologist via a user interface regarding the computer-aided diagnosis; and
selectively updating one or more of the baseline neural network model, the geographic model, the institution model, and the radiologist model based on the feedback.

2. The method of claim 1, further comprising receiving, from the radiologist via the user interface, a diagnosis for the medical image, wherein selectively updating the one or more of the radiologist model, the institution model, and the geographic model based on the medical image comprises selectively updating the one or more of the radiologist model, the institution model, and the geographic model based on the diagnosis and the medical image.

3. The method of claim 2, further comprising evaluating a performance of the radiologist model based on the diagnosis and the computer-aided diagnosis, wherein selectively updating the one or more of the radiologist model, the institution model, and the geographic model comprises updating the radiologist model based on the medical image and the diagnosis responsive to the performance of the radiologist model below a performance threshold for the radiologist model.

4. The method of claim 1, further comprising generating a second computer-aided diagnosis with a second radiologist model associated with a second radiologist, and displaying, to the radiologist via the user interface, the second computer-aided diagnosis.

5. The method of claim 1, further comprising training the baseline neural network model on diagnostic decisions of a second subset of the plurality of radiologists corresponding to a second geographic region to generate a second geographic model, training the second geographic model on diagnostic decisions of a subset of the second subset of the plurality of radiologists corresponding to a second institution in the second geographic region to generate a second institution model, and training the second institution model on diagnostic decisions of a second radiologist of the plurality of radiologists, the second radiologist associated with the second institution in the second geographic region, to generate a second radiologist model.

6. The method of claim 5, further comprising receiving a request for a second opinion from the second radiologist of the plurality of radiologists, and transmitting the request to a computing system of the second institution.

7. The method of claim 6, further comprising receiving, from the computing system of the second institution, a second computer-aided diagnosis generated to provide the second opinion as a digital twin of the second radiologist by the second radiologist model for the second radiologist, and displaying the second computer-aided diagnosis to the radiologist.

8. The method of claim 1, wherein selectively updating one or more of the baseline neural network model, the geographic model, the institution model, and the radiologist model based on the feedback comprises evaluating a performance of each of the baseline neural network model, the geographic model, the institution model, and the radiologist model with regard to the feedback, and selectively updating one or more of the baseline neural network model, the geographic model, the institution model, and the radiologist model responsive to the performance below a respective performance threshold, wherein the computer-aided diagnosis for the patient comprises analysis of a medical image acquired by an imaging system, and wherein the imaging system comprises a display device for displaying the medical image.

9. The method of claim 1, further comprising evaluating a performance of the radiologist model with respect to a performance of the institution model, the geographic model, and the baseline neural network model to identify a divergence of the radiologist model from one or more of the institution model, the geographic model, and the baseline neural network model.

10. A method, comprising:
 executing instructions in non-transitory memory storing a plurality of neural network models initially trained on diagnostic decisions of a plurality of radiologists via a processor in a computing system, wherein the instructions cause the processor to institute:
  training a baseline neural network model on diagnostic decisions of the plurality of radiologists;
  training the baseline neural network model on diagnostic decisions of a subset of the plurality of radiologists corresponding to a geographic region to generate a geographic model;
  training the geographic model on diagnosis decisions of a subset of the subset of the plurality of radiologists corresponding to an institution in the geographic region to generate an institution model, wherein a scope of a geographic area in the geographic model is determined according to differences in diagnostic protocols between geographic areas;
  training the institution model on diagnostic decisions of a radiologist of the plurality of radiologists, the radiologist associated with the institution in the geographic region, to generate a radiologist model;
  generating, with the radiologist model, a computer-aided diagnosis for a patient;
  displaying the computer-aided diagnosis for the patient;
  receiving feedback from a radiologist via a user interface regarding the computer-aided diagnosis; and
  selectively updating one or more of the baseline neural network model, the geographic model, the institution model, and the radiologist model based on the feedback, wherein the baseline neural network model, the geographic model, the institution model, and the radiologist model together form an ensemble of deep neural network models that maintain ensemble-level coherence for a radiologist ecosystem.

11. The method of claim 10, wherein a hierarchy in the ensemble is continuously updated based on feedback through corrections to outputs of the ensemble and corrections to diagnoses of radiologists.

12. The method of claim 10, wherein the computer-aided diagnosis for the patient is a radiologist-specific digital twin diagnosis.

13. The method of claim 1, wherein the computer-aided diagnosis for the patient is a digital twin diagnosis personalized to radiologists at the institution.

14. The method of claim 13, wherein an institution of the radiologist providing the feedback via the user interface is different than the institution for the digital twin diagnosis.

15. The method of claim 1, further comprising evaluating a performance of the radiologist model with respect to one or more of the institution model and the geographic model.

16. The method of claim 1, further comprising duplicating the baseline model and deploying the duplicated baseline model to form additional geographic models, additional institution models, and additional radiologist models.

17. The method of claim 16, further comprising:
 evaluating a performance of the radiologist model relative to a performance of the institution model and a performance of the geographic model, wherein the radiologist model is associated with a first radiologist at the institution, and wherein the baseline neural network model, the geographic model, the additional geographic models, the institution model, the additional institution models, the radiologist model, and the additional radiologist models together form an ensemble of deep neural network models;
 detecting the radiologist model is outperforming with respect to other radiologists associated with the additional radiologist models; and
 propagating the performance of the radiologist model throughout the ensemble.

18. The method of claim 17, wherein each of the radiologist model and the additional radiologist models are associated with a specific radiologist.

* * * * *